United States Patent [19]

Theodoropulos

[11] Patent Number: 4,810,782
[45] Date of Patent: Mar. 7, 1989

[54] DI-UREADOPYRIDINES AND THEIR CHELATES

[76] Inventor: Spyros Theodoropulos, 2964 Hickory St., Yorktown Heights, N.Y. 10598

[21] Appl. No.: 115,386

[22] Filed: Nov. 2, 1987

Related U.S. Application Data

[63] Continuation-in-part of Ser. No. 000,569, Dec. 23, 1986, abandoned.

[51] Int. Cl.$^4$ .......................... C07F 5/00; C07F 9/80; C07F 13/00
[52] U.S. Cl. ........................................ 534/15; 546/2; 544/64
[58] Field of Search ................. 546/2; 534/15; 544/64

[56] References Cited

PUBLICATIONS

Kumar et al. Chem. Abstracts, vol. 101,; 171864t (1984).

Primary Examiner—Mary C. Lee
Assistant Examiner—J. Richter
Attorney, Agent, or Firm—Burgess, Ryan & Wayne

[57] ABSTRACT

Novel chelates of 2,6-diureadopyridines and certain metal ions are provided which exhibit exceptional fluorescent characteristics when such chelates are exposed to incident or X-ray irradiation.

7 Claims, No Drawings

DI-UREADOPYRIDINES AND THEIR CHELATES

This application is a continuation-in-part of U.S. patent application Ser. No. 000,569, filed Dec. 23, 1986, now abandoned the entire contents of which is incorporated herein by reference.

FIELD OF THE INVENTION

This invention relates in general to di-ureadopyridines and chelates thereof with certain transition metals. In one aspect this invention relates to 2,6-diureadopyridines and transition metal chelates. In another aspect, this invention relates to 2,6-diureadopyridines which are useful in the preparation of transition metal chelates. In a further aspect this invention is directed to methods for preparation of the novel 2,6-diureadopyridines and chelates, and their use in applications wherein the fluorescent properties of such chelates are utilized, particularly in X-ray imaging techniques.

BACKGROUND OF THE INVENTION

It is known that chelating agents such as ethylenediaminetetraacetic acid (EDTA), 1,3-diketones and thiosemicarbazides, among others, form chelates with metal ions. However, of the known chelates few have been shown to exhibit fluorescence and more particularly, fluorescence produced by X-ray irradiation.

It is known that certain compounds such as for example fluorescein, coumarin, rhodamine and the like, contain groups which exhibit fluorescence when excited with incident light. It is also known that a few of these compounds or dyes, such as fluorescein isothiocyanate, have been used in analytical techniques for the determination and measurement of biological compounds of interest. However, there are various disadvantages associated with the prior art dyes that are employed in analytical techniques involving fluorescein. The fluorescence produced by conventionally employed dyes have limited excitation/emmision spectra, low quantum yields, high background fluorescence and, most importantly, such dye complexes are not permanent but fade and bleach.

Accordingly, one or more of the following objects will be achieved by the practice of the present invention. It is an object of this invention to provide 2,6-diureadopyridines and certain transition metal ion chelates which exhibit stable, fluorescence. Another object of this invention is to provide novel chelates which will exhibit distinct fluorescence exitation and emission spectra, corresponding to that of the specific metal ion that is chelated and wherein the chelates themselves are stable. It is a further object of the present invention to provide a process for simply and rapidly producing complexes of 2,6-diureadopyridines and metal ions which fluoresce when they are exposed to incident light. It is also an object of this invention to produce novel chelates of 2,6-diureadopyridines and transition metal ions. A further object of this invention is to provide chelates of 2,6-diureadopyridines which exhibit fluorescence upon X-ray irradiation. A still further object of this invention is to provide a method of X-ray imaging development utilizing the chelates of the present invention. A still further object of this invention is to provide chelates which will exhibit distinct fluorescence exitation and emission spectra corresponding to that of the specific metal ion which is chelated with the diureadopyridine when such compounds are exposed to X-ray radiation. Yet another object is to provide chelates of metal ions which are stable and which exhibit fluorescence without fading or bleaching. These and other objects will readily become apparent those skilled in the art in the light in the teachings set forth.

SUMMARY OF THE INVENTION

In its broad aspect, this invention is directed to 2,6-diureadopyridines, certain chelates of the 2,6-diureadopyridines with transition metals, and to processes for their preparation and use. The present invention is particularly directed to chelates formed between 2,6-diureadopyridines and metal ions of transition metals. These chelates will fluoresce upon exposure to incident light and X-rays due to the complexes formed between the 2,6-diureadopyridines and transition metals, especially those metals of the lanthanide series. The chelates of the present invention are advantageous when they exhibit fluorescence due to contacted with incident light as well as when they are excited with X-ray irradition.

DETAILED DESCRIPTION OF THE INVENTION

The 2,6-diureadopyridines employed in the present invention have the structural formula I:

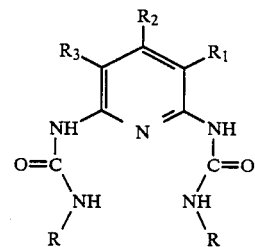

wherein R represents a substituted or unsubstituted hydrocarbon group of from 1 to 20 carbon atoms; or a substituted or unsubstituted alkyl, aryl or heterocyclic group of up to 20 carbon atoms; and $R_1$–$R_3$ represent hydrogen, Fl, Cl, Br, I, $NO_2$, NO, COOH, $SO_3H$, $NH_2$, $NHNH_2$, or a substituted or unsubstituted aryl, or heteroaryl group of up to 20 carbon atoms. Preferred 2,6-diureadopyridines which can be employed in the practice of the present invention are those wherein R represents alkyl or alkenyl of from 1 to 12 carbon atoms and $R_1$–$R_3$ are as indicated. Also preferred are those ureadopyridines wherein R represents aryl and cycloalkyl of up to 12 carbon atoms.

By the term "heteroaryl", or "heterocyclic" as used throughout the specification and appended claims is meant those groups composed of carbon, hydrogen and at least one member of the group of oxygen, nitrogen or sulfur. The preferred heterocyclic and heteroaryl groups are those derived from compounds such as pyridine, quinoline, benzothiazole, benzoxozole, morpholine, piperidine tetrahydropyrrole, and the like.

As indicated above, the R group of the 2,6-diureadopyridine can be substituted or unsubstituted with one or more groups which do not adversely affect the ability of the pyridine compound to form a stable chelate with a metal ion. Such substituents include among others, groups such as branched aliphatic groups, such as branched alkyl groups, alkoxy, acyl, thioalkoxy, alkylthio, alkylamino, dialkylamino, and the like.

The 2,6-diureadopyridines of the present invention were synthesized using conventional techniques and from readily available starting materials. For example, 2,6-diaminopyridine of the general formula:

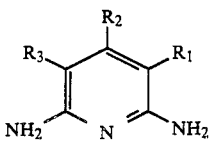

can be reacted with an isocyanate of the general formula:

$$R-N=C=O$$

wherein R and $R_1$–$R_3$ are as indicated above. An example is illustrated in the following equation:

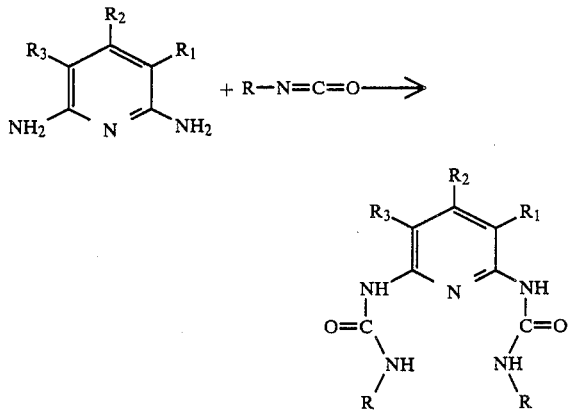

For example, a 2,6-diureadopyridine having unsaturated pendant groups is conveniently formed by using an unsaturated isocyanate and the appropriate 2,6-diaminopyridine:

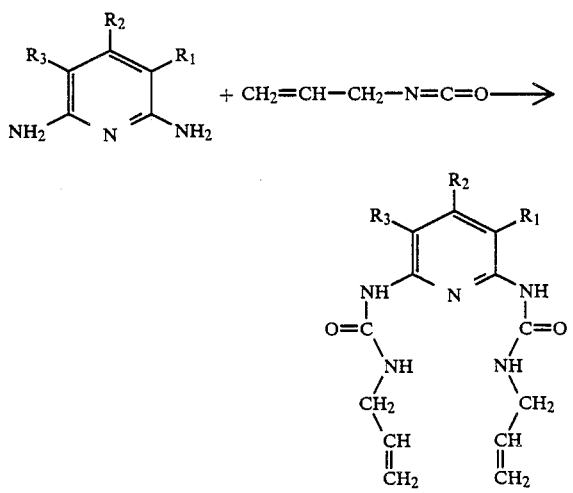

The synthesis was optionally performed in the presence of a solvent which was inert to the reactants and reaction products, such as aromatic hydrocarbons, esters, ketones, amides, pyridine and the like.

Temperature is not necessarily critical and those employed in the synthesis of the diureadopyridines ranged from about 5 to about 100° C., with ambient temperature being preferred.

The reaction of the pyridine with the isocyanate can be conducted at atmospheric pressure or at elevated or subatmospheric pressures.

After the preparation of the diureadopyridine compound the chelate with the transition metal ion can be conveniently effected by conventional procedures. In practice, the chelates are formed by reacting the diureadopyridine with a salt of the metal ion under conditions which promote the formation of a complex between the two reactants. A wide variety of metal salts of the transition metals can be utilized in the practice of the present invention. The only requirement of the metal salt is that it can be one which will form the metal chelate with the diureadopyridine and will not adversely affect the fluorescent properties of the final chelated compound. Salts which can be employed include, but is not limited to the inorganic salts such as the chlorides, nitrates, sulfates and the like, and organic salts such as metal alkoxy salts and the like.

As previously indicated the metals which are combined with the diureadopyridine compounds are the transition metals as set forth in the Periodic Table of Elements. In particular, the metals of the lanthanide series are preferred. Accordingly, suitable ions for chelating the compounds of the invention are ions of transition metals such as lanthanum, europium, scandium, indium, terbium, gandolinium, cerium, cobalt and gallium ions. It was preferred to use a lanthanum ion due to its ability to fluoresce when complexed with the diureadopyridine.

Preparation of the chelates of the ureadopyridines and the metal ions is effected in the conventional manner for the preparation of chelation compounds. In practice, this can be accomplished by contacting the pyridine with an appropriate metal ion salt in an inert, liquid medium. As shown in the examples, the diureadopyridine and a metal salt was mixed in the an inert liquid, such as methanol, and stirred at room temperature.

The 2,6-diureadopyridines of this invention being receptive to chelation, may be advantageously utilized in any of the several known techniques involving fluorescence generated by incident light or with X-ray radiation.

As indicated above, the 2,6-diureadopyridines of the present invention complex with metal ions preferably transition metal ions forming tridentate, pentadentate or heptadentate chelates depending on the nature of the R group. Chelates of lanthanum exhibit fluorescence both with incident and X-ray radiation.

The novel compounds of this invention are intended for use in a variety of systems which utilize the change in electronic properties of a compound due to the exposure of such compound to incident light or X-ray radiation and wherein such change can be recorded or visually observed. The chelates of this invention are therefore useful as imaging agents or as analytical agents and are particularly useful in X-ray development and imaging techniques utilizing X-ray irradiation or incident light.

The following examples illustrate the best mode presently contemplated for the practice of this invention.

EXAMPLE 1

N',N'(DIBUTYL)-2,6-DIUREADOPYRIDINE 1.09 grams of 2,6-diaminopyridine and 3.0 grams of butyl isocyanate were mixed in 5 milliliters of pryidine and the mixture stirred at ambient temperature overnight. The solvent was then removed in vacuo and the product washed with methanol. There was obtained 2.50 grams of a white solid product having a melting point of 220°–222° C. IR analysis (Nujol) showed bands at 3360 (NH), 3240 (NH), 1670, 1660, 1550, 1490, 1450, 1375, 1280, 1270, 1260, 1155 and 800 cm−1.

EXAMPLE 2

PREPARATION OF TERBIUM CHELATES WITH N,N'-DIBUTYL-2,6-DIUREADOPYRIDINE 100 milligrams of N,N'-dibutyl-2,6-diureadopyridine and 124 milligrams of terbium trichloride hexahydrate were mixed in 5 milliters of methanol and stirred for 5 minutes until a homogeneous solution occured. Removal of the solvent in vacuo left an oily material which solidified on standing. I.R. (nujol) showed bands at 3325, 2960, 1650, 1600, 1435, 1286, 1210, 1170 and 80 cm−1. Solutions of this chelate in methanol exhibited intense green fluorescence with incident light, Ex 368 nm, and Em 543 nm. Solution of this chelate in methanol exhibited intense green fluorescence with X-ray radiation.

EXAMPLE 3

N',N'-DIBUTYL-2,6-DIUREADO-3-NITROSOPYRIDINE 280 milligrams of 2,6-diamino-3-nitroso-pyridine and 1 milliter (excess) of n-butyl isocyanate were mixed in 5 milliliters of pryidine and the mixture stirred at ambient temperature for 24 hours. The solvent was then removed in vacuo and the product washed with acetone. Infrared analysis showed bands at 3300 (NH), 3160 (NH), 1686 (urea carbonyl), 1610, 1500, 1420, 1360, 1345, 1270, 1230, 1220, 1180, 1150,

EXAMPLE 4

PREPARATION OF N',N'-DICARBOXYETHYL-2,6-DIUREADOPYRIDINE

Structure:

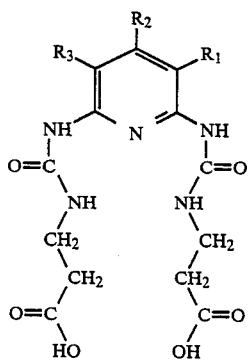

100 milligrams of 2,6-diaminopyridine and 0.5 milliliters of 3-isocyanatopropionic acid trimethyl silyl ester, were mixed in 5 milliliters of dry pyridine and the mixture was stirred at ambient temperature for 48 hours. The solvent was then removed under reduced pressure and the crude reaction mixture was washed with ether. Crystallization from methanol afforded 500 milligrams of the product having a melting point of 102°–105° C.

Although the invention has been illustrated by the preceding examples it is not to be construed as being limited to the materials employed therein, but rather, the invention encompasses the generic area as hereinbefore disclosed. Various modifications and embodiments thereof can be made without departing from the spirit or scope thereof.

What is claimed is:

1. Ureadopyridine chelates of:
   (a) a 2,6-diureadopyridine of the formula:

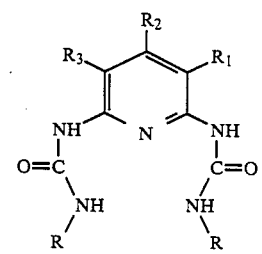

(b) a transition metal ion,
   wherein R represents a substituted or unsubstituted hydrocarbon group of from 1 to 20 carbon atoms; or a substituted or unsubstituted heterocyclic group of up to 20 carbon atoms; and $R_1$–$R_3$ represent hydrogen, F, Cl, Br, I, $NO_2$, NO, COOH, $SO_3H$, $NH_2$, $NHNH_2$, or a substituted or unsubstituted aryl, or heteroaryl group of up to 20 carbon atoms, said heterocyclic and heteroaryl groups being composed of carbon, hydrogen and at least one member of the group consisting of oxygen, nitrogen and sulfur.

2. Ureadopyridine chelates of:
   (a) a 2,6-diureadopyridine of the formula:

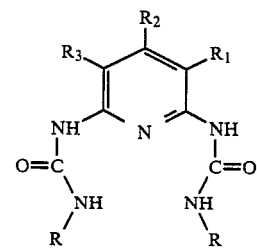

(b) a transition metal ion,
   wherein R represents alkyl of from 1 to 20 carbon atoms and $R_1$–$R_3$ represent hydrogen.

3. The diureadopyridine chelate of claim 2 wherein R represents butyl and $R_1$–$R_3$ represent hydrogen.

4. The diureadopyridine chelate of claim 1 wherein the transition metal ion is a lanthanide.

5. The diureadopyridine chelate of claim 1 wherein the transition metal ion is terbium.

6. The diureadopyridine chelate of claim 1 wherein the transition metal ion is europium.

7. The diureadopyridine chelate of claim 1 wherein the transition metal ion is indium.

* * * * *